United States Patent [19]
Yamano et al.

[11] Patent Number: 5,238,814
[45] Date of Patent: Aug. 24, 1993

[54] IGG ANTIGEN-ANTIBODY COMPLEX FOR QUICK RH BLOOD TYPING

[75] Inventors: Hajime Yamano, Mie; Toru Nakade, Nara; Hideo Takahashi; Harumichi Matsukura, both of Osaka; Yasuto Okubo, Nara, all of Japan

[73] Assignee: Sanko Junyaku Co., Ltd., Tokyo, Japan

[21] Appl. No.: 817,509

[22] Filed: Jan. 7, 1992

Related U.S. Application Data

[63] Continuation-in-part of Ser. No. 450,178, Dec. 13, 1989, abandoned, which is a continuation-in-part of Ser. No. 133,387, Dec. 15, 1987, abandoned.

[51] Int. Cl.$^5$ ............... C12Q 1/02; G01N 33/531
[52] U.S. Cl. ...................... 435/7.25; 424/11; 435/7.2; 436/513; 436/536
[58] Field of Search ............ 436/513, 536, 63; 435/7.2, 7.25; 424/11

[56] References Cited

PUBLICATIONS

Hughes-Jones et al.-Vox Sang. vol. 53(3) (1987) pp. 175-180.

*Primary Examiner*—Sam Rosen
*Attorney, Agent, or Firm*—Kanesaka & Takeuchi

[57] ABSTRACT

An antigen-antibody complex in which two molecules of IgG class monoclonal anti-D are bound to one or two molecules of monoclonal or polyclonal anti-IgG antibody specific to the IgG class monoclonal anti-D. It reacts with Rh(D) positive blood cells, causing an observable agglutination and is useful for quick Rh blood typing.

5 Claims, 2 Drawing Sheets

IGG ANTIGEN-ANTIBODY COMPLEX FOR QUICK RH BLOOD TYPING

CROSS-REFERENCE TO RELATED APPLICATIONS

This application is a continuation-in-part of Ser. No. 450,178 filed Dec. 13, 1989, which is a continuation-in-part of Ser. No. 133,387 filed Dec. 15, 1987, both now abandoned.

BACKGROUND OF THE INVENTION

The present invention relates to an antigen-antibody complex and a method of using the same as an agglutination reagent.

One of the conventional reagents for use in testing the Rh blood type is a monoclonal human anti-D antibody (hereinafter "monoclonal human anti-D"). The production and the use of this monoclonal human anti-D are described in the Proceedings of the 13th Japanese society for Immunology (1983), pp. 416-417, and Japanese Patent Application Kokai Nos. 58-500,366, 59-138,959, and 60-70,361. Another reagent is a polyclonal human anti-D obtained from the human serum. This is a commonly used, officially licensed reagent.

However, the reactivity of the above monoclonal antibody with the corresponding antigen is so low that the antibody is useful for only a few testing methods. For the Rh blood typing, for example, these are an anti-human globulin testing method, a bromelain solution method, an albumin solution method, and a physiological saline solution method. The monoclonal human anti-D presented in the 13th Japanese Society for Immunology is able to cause agglutination by the anti-human globulin testing or bromelain solution method and determined the blood type of an Ph(D) antigen but unable to cause any agglutination by the albumin or saline solution method, thus putting a limit on its applicability.

The polyclonal human anti-D antibody is a human origin reagent using human serum or its dilution with a proper diluent and it is difficult to produce it in large amounts because the human serum is obtained usually by administering Rh negative persons with the Rh positive blood.

SUMMARY OF THE INVENTION

Accordingly, it is an object of the invention to provide an agglutination reagent useful for various applications, especially various blood typing methods.

In attempts to solve the above problems with the monoclonal antibody, we have discovered that an IgG antigen-antibody complex solution made by combining tow molecules of IgG class monoclonal human anti-D antibody specific to a human Rh(D) antigen with one or two molecules of monoclonal or polyclonal anti-human IgG antibody specific to the IgG class monoclonal human anti-D antibody is useful as a quick red blood cell agglutination reagent.

One advantage of the invention is that with the IgG antigen-antibody complex of the invention, an agglutination occurs very fast by one step reaction so that it is possible to determined the Rh(D) blood type instantly.

The above and other objects, features, and advantages of the invention will be more apparent from the following description when taken in conjunction with the accompanying drawings.

DESCRIPTION OF THE PREFERRED EMBODIMENT

Figure 1:
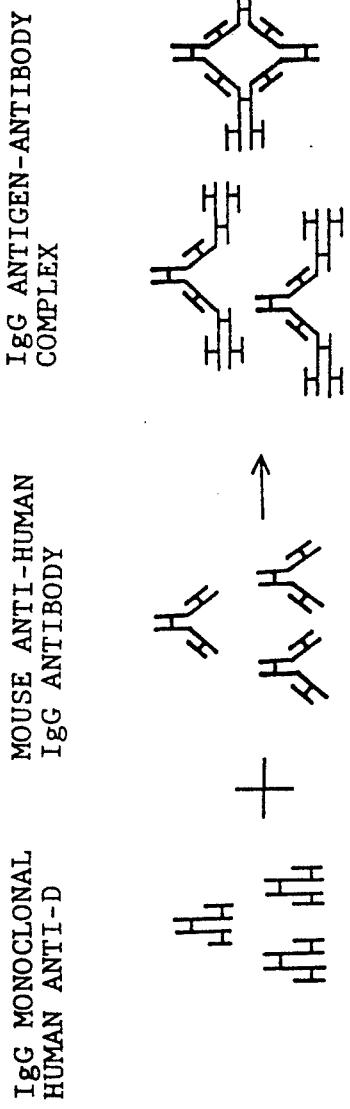
FIG. 1 shows the production of an IgG antigen-antibody complex according to an embodiment of the invention.

The IgG class monoclonal antibody, which has been used for determining the red blood cell surface antigen (blood type substance), is an antibody for the blood type. According to an embodiment of the invention, the IgG class monoclonal human anti-D is bound to a monoclonal or polyclonal anti-human IgG antibody as shown in FIG. 1. That is to say, an IgG class monoclonal human anti-D and a monoclonal or polyclonal anti-human IgG antibody are bound to form an IgG antigen-antibody complex solution in which two molecules of the IgG class monoclonal human anti-D are bound to one or two molecules of the monoclonal or polyclonal anti-human IgG antibody.

Figure 2:
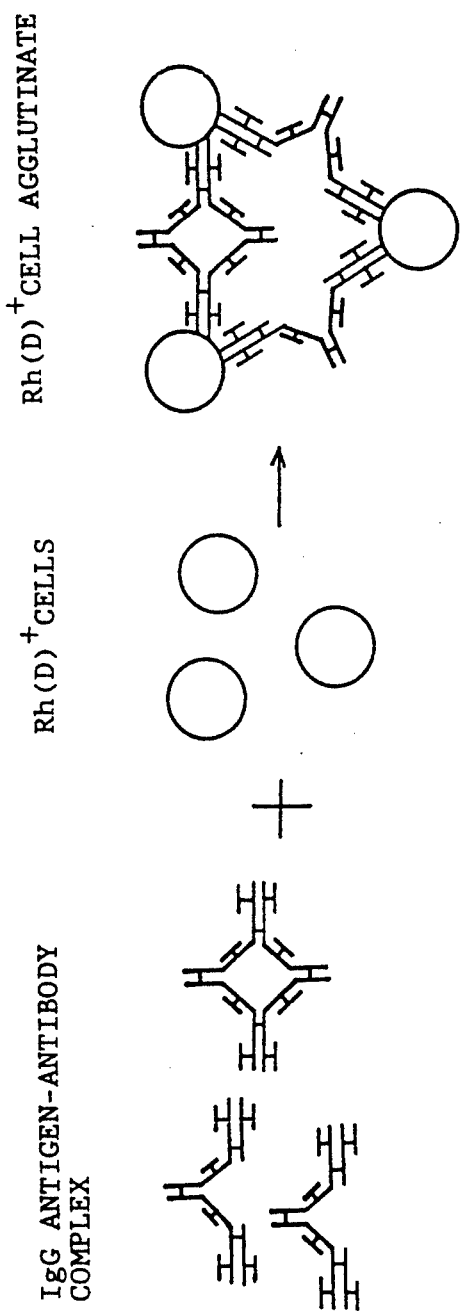
FIG. 2 shows agglutination of Rh(D) positive cells by the IgG antigen-antibody complex of FIG. 1.

When this antigen-antibody complex is added to an Rh(D) antigen (human red blood cells) to be detected, the binding site anti-D of the IgG antigen-antibody complex is bound to the Rh(D), causing an agglutination as shown in FIG. 2. This agglutination is easy to observe for detection of the Rh(D).

Figure 3:
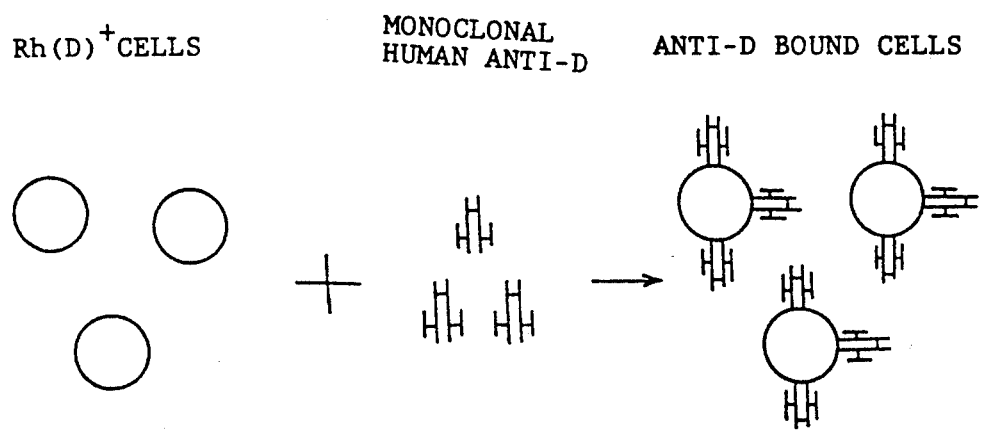
FIGS. 3 and 4 show the use of a conventional monoclonal antibody in an anti-human globulin test.
Figure 4:
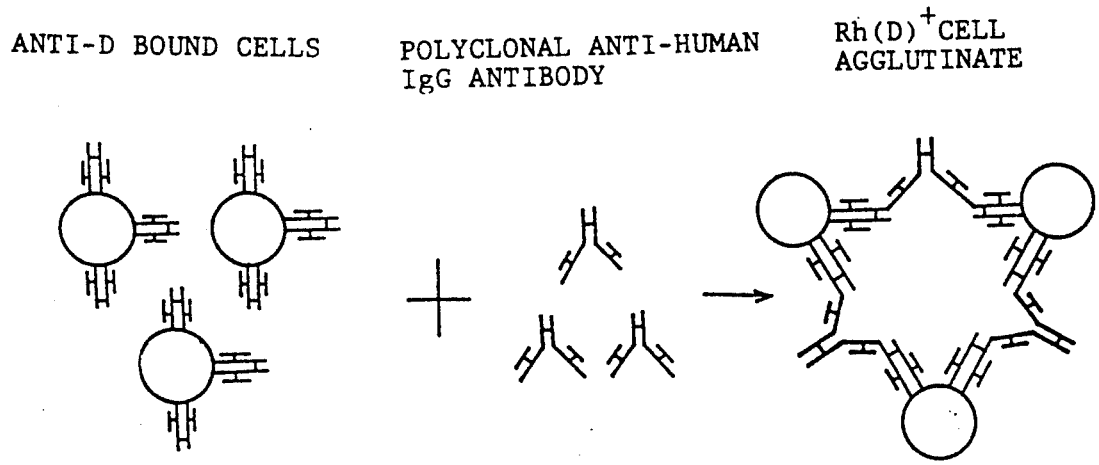

FIGS. 3 and 4 show the agglutination of an anti-human globulin test for detecting an Rh(D) blood antigen by using a conventional monoclonal human anti-D. In FIG. 3, a monoclonal human anti-D is added to the Rh(D) positive blood cell and incubated at 37 degrees C. for tens of minutes so that the binding site of the monoclonal human anti-D is bound to the Rh(D) antigen or Rh(D) positive blood cell to form an anti-D antibody bound blood cell.

Since this is unable to be seen as an agglutination, an anti-human globulin serum or polyclonal anti-human IgG antibody is added so that the binding site of the polyclonal anti-human IgG antibody is bound to the monoclonal human anti-D, causing an observable agglutination as shown in FIG. 4.

In contrast to the above, when the IgG antigen-antibody complex of the invention is used, an agglutination is formed by only one step reaction so that the blood type is able to determined at once.

EXAMPLE 1

In this example, a monoclonal human anti-D and a monoclonal mouse anti-human IgG antibody are used as the IgG class antibody and the anti-human IgG antibody, respectively.

(1) Production of the Monoclonal Human Anti-D

Peripheral lymph cells of an Rh(D) negative person with an anti-D antibody were infected with an Epstein-Barr virus (EBV). The transformed cells were cloned in a soft agar culture medium to form a monoclonal human anti-D strain (B2-1 strain). This procedure is described by Masatsune Uno et al. in the Proceedings of the 13th Japanese Society for Immunology (1983), pp. 416-417.

The thus cloned B2-1 strain and a JMS-3 strain are fused in polyethylene glycol 1500 (PEG-1500). The fused cells were cloned by limiting dilution techniques to form a monoclonal human anti-D producing strain (B-7-D-10 strain). This anti-D was purified by separating the IgG fraction by a 50% saturated ammonium sulfate salting out method and selecting an IgG class monoclonal human anti-D with 0.0175 Mol phosphate buffered saline solution (PBS), pH 6.8, using diethylaminoethyl cellulose (DEAE Sephacell, Pharmacia Co.).

(2) Production of the Monoclonal Anti-Human IgG Antibody

A BALB/C mouse was immunized with the human IgG obtained by purifying human serum with DEG-4000 with mouse myeloma cells (P3-X63-Ag8-U strain) derived from the BALB/C mouse. The fused cells were cloned by limiting dilution techniques to form a monoclonal anti-human IgG antibody producing strain according to the method described by Takeshi Watanabe in Immunology Experimental Procedures IX (1978), P. 2963. The IgG antibody was purified in the same manner as in (1) above the provide an anti-human IgG antibody. The molecular weight of the IgG fraction antibody is no more than about 150,000.

(3) Determination of Titer of the Monoclonal Human Anti-D 0.1 ml of the anti-D obtained in (1) above was diluted serially twice with a physiological saline solution. A suspension of 2% Rh(D) positive cells in saline was added by dropping to the dilution for reaction at 37 degrees C. for 60 minutes. After the reaction product was washed with saline three times, two drops of anti-human globulin serum was added to it and the mixture was centrifuged at 3400 rpm for 15 seconds. The maximum dilution magnification showing agglutination was taken as the titer.

(4) Determination of Titer of the Monoclonal Mouse Anti-Human IgG Antibody 0.1 ml of the monoclonal anti-human IgG antibody obtained in (2) above was diluted serially twice with a diluent containing 3% fetal bovine serum (FBS) and 0.1% $NaN_3$ in saline. A 2% anti-D bound cell saline, which had been prepared by mixing a volume of 2% suspension of "$R_1R_2$" (Rh phenotype CcDEe) cells in saline with a volume of anti-D serum (albumin antibody) diluted 100 times with saline and incubating the mixture at 37 degrees C. for one hour, was added by dropping to the dilution. The mixture was centrifuged at 3400 rpm for 15 seconds. The maximum dilution magnification showing agglutination was taken as the titer.

(5) Production of the IgG Antigen-Antibody Complex

The monoclonal human anti-D obtained in (1) above was diluted with a 0.013 Mol PBS, pH 7.0, containing 2% bovine albumin and 0.1% $NaN_3$ so that it had a titer of 4096 in the indirect anti-globulin test with Rh(D) positive cells. The monoclonal anti-human IgG antibody obtained in (2) above was adjusted to have a titer of 256 as in (4) above. Equal volumes (40 ug/ml and 32 ug/ml respectively) of these dilutions were mixed and incubated at 37 degrees C. for one hour to form an IgG antigen-antibody complex in which two molecules of the IgG class monoclonal human anti-D were bound to one or two molecules of the monoclonal mouse anti-human IgG antibody specific to the above antibody. See FIG. 1.

(6) Use of the IgG Antigen-Antibody Complex as an Rh Blood Type Assay

The IgG antigen-antibody complex obtained in (5) above was brought into contact with Rh(D) positive cells for reaction, making a conspicuous agglutination in about 10–15 seconds. See FIG. 2.

TABLE 1

| Cells Rh Expression | | No. of Cases | Saline Method | |
|---|---|---|---|---|
| | | | MHAD*1 | CMPLX*2 |
| Rh(D) Positive | | 800 | (−) | + + + + |
| Rh(D) Negative | ccdEE | 7 | (−) | (−) |
| | ccdEe | 12 | (−) | (−) |
| | Ccdee | 5 | (−) | (−) |
| | ccdee | 8 | (−) | (−) |

*1 - Monoclonal Human Anti-D
*2 - IgG Antigen-Antibody Complex of the Invention

TABLE 2

| Cells Rh Expression | | No. of Cases | CMPLX*1 | ASTM*2 |
|---|---|---|---|---|
| Rh(D) Positive | | 800 | + + + + | + + + + |
| Rh(D) Negative | ccdEE | 7 | (−) | (−) |
| | ccdEe | 12 | (−) | (−) |
| | Ccdee | 5 | (−) | (−) |
| | ccdee | 8 | (−) | (−) |

*1 - IgG Antigen-Antibody Complex of the Invention by Saline Solution Method
*2 - Polyclonal Anti-D Serum (Ortho Diagnostic Systems, Inc.) by Albumin Solution Method.

Table 1 above shows the test results using a conventional monoclonal human anti-D and the IgG antigen-antibody complex of the invention by the saline solution method. It indicates that the antigen-antibody complex of the invention exhibited a strong agglutination, but the monoclonal human anti-D did not show any agglutination.

Table 2 above shows the test results on the same samples as the above using a polyclonal anti-D serum by the albumin solution method and the IgG antigen-antibody complex of the invention by the saline solution method. Both reagents showed strong agglutination with Rh(D) positive cells, indicating the IgG antigen-antibody complex was effective for determining the Rh blood type.

EXAMPLE 2

In this example, a monoclonal human anti-D and a polyclonal anti-human IgG antibody were used as the IgG class antibody and the polyclonal anti-IgG antibody, respectively.

(1) Production and Titer Determination of a Monoclonal Human Anti-D

These processes were carried out in the same manner as in (1) and (3) of Example 1, respectively.

(2) Production of Polyclonal Anti-Human IgG Antibody

The IgG fraction was separated from normal human serum by a 50% saturated ammonium sulfate salting out method and purified by DEAE Sephacell ion exchange chromatography. This purified IgG was inoculated into a rabbit. After different agglutinins were absorbed with neuraminidase treated human cells, the IgG fraction was separated from the resulting antiserum by a 50% saturated ammonium sulfate salting out method and purified with DEAE Sephacell to provide a polyclonal anti-human IgG antibody. The molecular weight of the IgG fraction antibody is no more than about 150,000.

(3) Titer Determination and Production of an IgG Antigen-Antibody Complex

These processes were carried out in the same manner as in (4) and (5) of Example 1, respectively. In the IgG antigen-antibody complex, two molecules of the IgG class monoclonal human anti-D were bound to one or two molecules of the polyclonal anti-IgG antibody. See FIG. 1.

(4) Use of the IgG Antigen-Antibody Complex as an Rh Blood Type Assay

The IgG antigen-antibody complex obtained in (3) above was brought into contact with Rh(D) positive cells for reaction, making conspicuous agglutination in about 10–15 seconds, while it showed no agglutination with Rh(D) negative cells.

Tables 3 and 4 below show the test results corresponding to Tables 1 and 2, respectively. From these tables, it is apparent that unlike the mere monoclonal human anti-D, the complex of the monoclonal human anti-D antibody and the polyclonal anti-human IgG antibody showed as strong agglutinations as in Example 1. See FIG. 1.

TABLE 3

| Cells Rh Expression | | No. of Cases | Saline Method | |
|---|---|---|---|---|
| | | | MHAD*1 | CMPLX*2 |
| Rh(D) Positive | | 760 | (−) | ++++ |
| Rh(D) Negative | ccdEE | 6 | (−) | (−) |
| | ccdEe | 12 | (−) | (−) |
| | Ccdee | 6 | (−) | (−) |
| | ccdee | 8 | (−) | (−) |

*1 - Monoclonal Human Anti-D
*2 - IgG Antigen-Antibody Complex of the Invention

TABLE 4

| Cells Rh Expression | | No. of Cases | CMPLX*1 | PAD*2 |
|---|---|---|---|---|
| Rh(D) Positive | | 760 | ++++ | ++++ |
| Rh(D) Negative | ccdEE | 6 | (−) | (−) |
| | ccdEe | 12 | (−) | (−) |
| | Ccdee | 6 | (−) | (−) |
| | ccdee | 8 | (−) | (−) |

*1 - IgG Antigen-Antibody Complex of the Invention by Saline Solution Method
*2 - Polyclonal Anti-D Serum (Ortho Diagnostic Systems, Inc.) by Albumin Solution Method.

This IgG antigen-antibody complex was able to agglutinate in various Rh blood typing methods, such as an anti-human globulin testing method, bromelain solution method, and albumin solution method, as well as a saline solution method.

The saline solution test method includes the steps of placing in a test tube 0.11 cc of the reagent according to the invention or human IgG class antigen-antibody complex specific to Rh(D); adding 0.1 cc of 2 v/v% saline solution suspension of test blood cells for forming mixture; and whirling the mixture in a centrifuge at 1000 rpm for one minute for observation of the resulting agglutination.

The anti-human globulin test method includes the steps of placing in a test tube 0.1 cc of the reagent according to the invention or human IgG class antigen-antibody complex specific to Rh(D) antigen; adding 0.1 cc of 2 v/v% saline solution of test blood cells for forming a mixture; washing the blood cells within the test tube with saline solution three times; adding 0.1 cc of anti-human globulin serum in the test tube for forming a mixture; and whirling the mixture in a centrifuge at 1000 rpm for one minute for observation of the resulting agglutination.

The albumin solution test method includes the steps of placing in a test tube 0.1 cc of the reagent according to the invention or human IgG class antigen-antibody complex specific to Rh(D); adding 0.1 cc of 2v/v% saline solution suspension of test blood cells and then 0.1 cc of 22% aqueous solution of bovine albumin for forming a mixture; and whirling the mixture in a centrifuge at 1000 rpm for one minute for observation of the resulting agglutination.

The bromelain solution test method or one-stage test method with bromelain includes the steps of placing in a test tube 0.1 cc of the reagent according to the invention or human IgG class antigen-antibody complex specific to Rh(D); adding 0.1 cc of 2 v/v% saline solution suspension of test blood cells and then 0.1 cc of 0.2 w/v% bromelain solution (made by dissolving bromelain in 0.15 ml phosphate buffered saline solution, pH 5.5, at a concentration of 0.2%) forming a mixture; heating the mixture at 37 degrees C. for 15 minutes; and whirling the mixture in a centrifuge at 1000 rpm for one minute for observation of the resulting agglutination.

Unlike the conventional polyclonal anti-D serum which produces no agglutinations with positive blood cells by the saline solution test method, the reagent according to the invention produces visible agglutinations. Although the conventional polyclonal anti-D serum can be used as a reagent for the anti-human globulin test method, the albumin solution test method, bromelain solution test method, the reagent according to the invention dramatically reduces the test time.

The conventional monoclonal antibody reagent has caused agglutination in only a few Rh blood typing methods and has been impractical. By contrast, the IgG antigen-antibody complex of the invention is useful as an Rh blood typing assay for all of the known blood typing methods by agglutination. In addition, it needs no human serum as polyclonal anti-D serum so that it is easy to obtain the materials.

We claim:

1. An IgG antigen-antibody complex solution specific for an Rh(D) antigen, which comprises:
    an IgG class human monoclonal anti-D antibody specific to a human Rh(D) antigen; and
    a mouse anti-human IgG antibody specific for said IgG class human monoclonal anti-D antibody.

2. The IgG antigen-antibody complex of claim 1, wherein said monoclonal IgG class human anti-D antibody and said monoclonal mouse anti-human IgG antibody are present in a molecular ratio of 2 to 1 or 2.

3. The IgG antigen-antibody complex of claim 1, wherein the molecular weight of said mouse anti-human IgG antibody is no more than about 150,000.

4. A method of detecting an Rh(D) blood type, which comprises the step of bringing said IgG antigen-antibody complex of claim 1 into contact with a volume of red blood cells by a saline solution, albumin solution, or bromelain solution method so that visible agglutinations are produced.

5. The method of claim 4, wherein said volume of red blood cells is a 2 v/v% suspension of red blood cells in a saline solution.

* * * * *